United States Patent
Meglan

(10) Patent No.: US 12,256,890 B2
(45) Date of Patent: Mar. 25, 2025

(54) SYSTEMS AND METHODS FOR GUIDING SURGICAL PROCEDURES

(71) Applicant: Covidien LP, Mansfield, MA (US)

(72) Inventor: Dwight Meglan, Westwood, MA (US)

(73) Assignee: Covidien LP, Mansfield, MA (US)

(*) Notice: Subject to any disclaimer, the term of this patent is extended or adjusted under 35 U.S.C. 154(b) by 378 days.

(21) Appl. No.: 17/779,146

(22) PCT Filed: Nov. 18, 2020

(86) PCT No.: PCT/US2020/060990
§ 371 (c)(1),
(2) Date: May 24, 2022

(87) PCT Pub. No.: WO2021/133483
PCT Pub. Date: Jul. 1, 2021

(65) Prior Publication Data
US 2022/0395334 A1    Dec. 15, 2022

Related U.S. Application Data

(60) Provisional application No. 62/952,628, filed on Dec. 23, 2019.

(51) Int. Cl.
*A61B 1/00* (2006.01)
*A61B 34/20* (2016.01)
(Continued)

(52) U.S. Cl.
CPC .... *A61B 1/000096* (2022.02); *A61B 1/00055* (2013.01); *A61B 34/20* (2016.02);
(Continued)

(58) Field of Classification Search
CPC .............. A61B 1/000096; A61B 34/20; A61B 1/00055; A61B 2034/2057; G06T 7/593;
(Continued)

(56) References Cited

U.S. PATENT DOCUMENTS 6,132,368 A   10/2000  Cooper
6,206,903 B1   3/2001  Ramans
(Continued)

FOREIGN PATENT DOCUMENTS

WO   2019130085 A1   7/2019
WO   2019130086 A1   7/2019

OTHER PUBLICATIONS

International Search Report mailed Apr. 9, 2021 and Written Opinion completed Mar. 30, 2021 corresponding to counterpart Int'l Patent Application PCT/US20/60990.
(Continued)

*Primary Examiner* — William D Titcomb
(74) *Attorney, Agent, or Firm* — Carter, DeLuca & Farrell LLP

(57) ABSTRACT

Methods for guiding a surgical procedure include accessing information relating to a surgical procedure, accessing at least one image of a surgical site captured by an endoscope during the surgical procedure, identifying a tool captured in the at least one image by a machine learning system, determining whether the tool should be changed based on comparing the information relating to the surgical procedure and the tool identified by the machine learning system, and providing an indication when the determining indicates that the tool should be changed.

20 Claims, 6 Drawing Sheets

(51) Int. Cl.
*G06T 7/00* (2017.01)
*G06T 7/593* (2017.01)
*G06T 7/70* (2017.01)
*G06V 20/50* (2022.01)

(52) U.S. Cl.
CPC ............ *G06T 7/0012* (2013.01); *G06T 7/593* (2017.01); *G06T 7/70* (2017.01); *G06V 20/50* (2022.01); *A61B 2034/2057* (2016.02); *G06T 2207/10012* (2013.01); *G06T 2207/10068* (2013.01); *G06T 2207/20081* (2013.01); *G06V 2201/034* (2022.01)

(58) Field of Classification Search
CPC ...................... G06T 7/70; G06T 7/0012; G06T 2207/10012; G06T 2207/10068; G06T 2207/20081; G06V 20/50; G06V 2201/034
USPC ......................................................... 382/128
See application file for complete search history.

(56) References Cited

U.S. PATENT DOCUMENTS

| | | | |
|---|---|---|---|
| 6,246,200 B1 | 6/2001 | Blumenkranz et al. |
| 6,312,435 B1 | 11/2001 | Wallace et al. |
| 6,331,181 B1 | 12/2001 | Tierney et al. |
| 6,394,998 B1 | 5/2002 | Wallace et al. |
| 6,424,885 B1 | 7/2002 | Niemeyer et al. |
| 6,441,577 B2 | 8/2002 | Blumenkranz et al. |
| 6,459,926 B1 | 10/2002 | Nowlin et al. |
| 6,491,691 B1 | 12/2002 | Morley et al. |
| 6,491,701 B2 | 12/2002 | Tierney et al. |
| 6,493,608 B1 | 12/2002 | Niemeyer |
| 6,565,554 B1 | 5/2003 | Niemeyer |
| 6,645,196 B1 | 11/2003 | Nixon et al. |
| 6,659,939 B2 | 12/2003 | Moll |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |

(56) References Cited

U.S. PATENT DOCUMENTS

| | | |
|---|---|---|
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Arkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,675,354 B2 | 6/2017 | Weir et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,383,694 B1 * | 8/2019 | Venkataraman ....... G16H 40/63 |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |

(56) References Cited

U.S. PATENT DOCUMENTS

| | | |
|---|---|---|
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Piolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 11,348,257 B2* | 5/2022 | Lang ................. A61B 34/25 |
| 11,647,888 B2* | 5/2023 | Meglan ............. H04N 13/344 |
| | | 348/53 |
| 11,801,114 B2* | 10/2023 | Lang ................. A61B 90/98 |
| 11,806,085 B2* | 11/2023 | Meglan ............. A61B 34/30 |
| 11,871,901 B2* | 1/2024 | Shelton, IV ......... G16H 40/67 |
| 11,925,423 B2* | 3/2024 | Meglan ............. A61B 34/30 |
| 11,986,261 B2* | 5/2024 | Meglan ............. G05D 1/0231 |
| 12,029,510 B2* | 7/2024 | Peine ............... A61B 34/32 |
| 12,048,413 B2* | 7/2024 | Tada ............... G06T 7/0016 |
| 2009/0088634 A1* | 4/2009 | Zhao ............... A61B 1/00193 |
| | | 600/425 |
| 2015/0287236 A1* | 10/2015 | Winne ............... G06T 15/08 |
| | | 382/128 |
| 2017/0251900 A1* | 9/2017 | Hansen ............... G06T 19/20 |
| 2019/0104919 A1* | 4/2019 | Shelton, IV ......... A61B 18/00 |
| 2019/0125361 A1* | 5/2019 | Shelton, IV ......... A61B 17/1227 |
| 2019/0125454 A1* | 5/2019 | Stokes ............... A61B 18/1206 |
| 2019/0125455 A1* | 5/2019 | Shelton, IV ......... A61B 5/061 |
| 2019/0125456 A1* | 5/2019 | Shelton, IV ......... A61B 17/072 |
| 2019/0125457 A1* | 5/2019 | Parihar ............. A61B 17/0206 |
| 2019/0125458 A1* | 5/2019 | Shelton, IV ......... A61B 17/072 |
| 2019/0200844 A1* | 7/2019 | Shelton, IV ......... H04L 67/10 |
| 2019/0200977 A1* | 7/2019 | Shelton, IV ......... A61B 34/35 |
| 2019/0200981 A1 | 7/2019 | Harris et al. |
| 2019/0201018 A1 | 7/2019 | Shelton, IV et al. |
| 2019/0201019 A1 | 7/2019 | Shelton, IV et al. |
| 2019/0201104 A1* | 7/2019 | Shelton, IV ......... A61B 90/98 |
| 2019/0201136 A1* | 7/2019 | Shelton, IV ......... A61B 1/051 |
| 2019/0201137 A1* | 7/2019 | Shelton, IV ......... G16H 50/20 |
| 2019/0206562 A1* | 7/2019 | Shelton, IV ......... A61M 1/79 |
| 2019/0206564 A1* | 7/2019 | Shelton, IV ......... A61M 1/79 |
| 2019/0380791 A1* | 12/2019 | Fuerst ............... G06F 3/0346 |
| 2020/0022764 A1* | 1/2020 | Flexman ............. G02B 6/022 |
| 2020/0078106 A1* | 3/2020 | Henderson ..... A61B 17/320092 |
| 2020/0081585 A1* | 3/2020 | Petre ................. A61B 90/361 |
| 2020/0135330 A1* | 4/2020 | Sugie ............... G06V 10/147 |
| 2020/0304753 A1* | 9/2020 | Venkataraman ... A61B 1/00045 |
| 2021/0030495 A1* | 2/2021 | Savall ............... A61B 34/20 |
| 2021/0290315 A1* | 9/2021 | Lampert ............. A61B 34/20 |
| 2021/0401508 A1* | 12/2021 | Zhao ............... A61B 6/463 |
| 2022/0020496 A1* | 1/2022 | Saito ............... G06T 7/0012 |

OTHER PUBLICATIONS

European Examination Report dated Nov. 13, 2023 for European Application No. 20824768.4-1216 (8 pages).

* cited by examiner

SYSTEMS AND METHODS FOR GUIDING SURGICAL PROCEDURES

CROSS-REFERENCE TO RELATED APPLICATIONS

The present application is a U.S. National Stage Application filed under 35 U.S.C. § 371(a) of International Patent Application Serial No. PCT/US2020/060990, filed Nov. 18, 2020, which claims the benefit of and priority to U.S. Provisional Patent Application Ser. No. 62/952,628, filed Dec. 23, 2019, the entire disclosure of each of which being incorporated by reference herein.

FIELD

The present technology is generally related to assisted surgical procedures and, more particularly, to systems and methods for guiding surgical procedures, such as in robotic surgical procedures.

BACKGROUND

During laparoscopic surgical procedures, an endoscope is used to visualize a surgical site. Particularly, in minimally invasive surgery (MIS) involving robotic surgery, image sensors have been used to allow a surgeon to visualize a surgical site.

A surgeon performing a laparoscopic surgery has a limited scope of view of the surgical site through a display. When a non-robotic tool, a robotic tool, or a laparoscopic instrument is used, the proper or appropriate selection and positioning of such tools for the surgical operation is based on the clinician's judgment and experience. When an inappropriate tool is used, for example, or when a tool is not appropriately positioned, the treatment results may be sub-optimal. There is interest in developing systems for supplementing a clinician's experience and judgment during surgical operations.

SUMMARY

The techniques of this disclosure generally relate to systems and methods for guiding a surgical procedure by supplementing a clinician's judgment and experience.

In an aspect, a method for guiding a surgical procedure includes accessing information relating to a surgical procedure, accessing at least one image of a surgical site captured by an endoscope during the surgical procedure, identifying a tool captured in the at least one image by a machine learning system, determining whether the tool should be changed based on comparing the information relating to the surgical procedure and the tool identified by the machine learning system, and providing an indication when the determining indicates that the tool should be changed.

In various embodiments of the method, the information relating to the surgical procedure indicates tools which have been used for other surgical procedures of a same type as the surgical procedure, and determining whether the tool should be changed includes determining whether the tool is among the tools which have been used for the other surgical procedures.

In various embodiments of the method, determining whether the tool should be changed includes determining that the tool should be changed when the tool is not among the tools which have been used for the other surgical procedures.

In various embodiments of the method, the endoscope is a stereo-endoscope, the at least one image includes at least one stereoscopic image, and the at least one stereoscopic image includes depth information relating to the tool and to tissue of the surgical site.

In various embodiments of the method, the method includes determining orientation information for the tool by the machine learning system based on the at least one image.

In various embodiments of the method, the machine learning system was trained using tool orientation information for other surgical procedures of a same type as the surgical procedure.

In various embodiments of the method, the orientation information for the tool determined by the machine learning system indicates whether the tool should be re-oriented.

In various embodiments of the method, the method includes determining position information for the tool by the machine learning system based on the at least one image.

In various embodiments of the method, the machine learning system was trained using tool position information for other surgical procedures of a same type as the surgical procedure.

In various embodiments of the method, the position information for the tool determined by the machine learning system indicates whether the tool should be re-positioned.

In an aspect, a surgical guiding system for guiding a surgical procedure includes a memory configured to store instructions, and a processor coupled with the memory and configured to execute the instructions. The processor is configured to execute the instructions to cause the surgical guiding system to access information relating to a surgical procedure, access at least one image of a surgical site captured by an endoscope during the surgical procedure, identify a tool captured in the at least one image by a machine learning system, determine whether the tool should be changed based on comparing the information relating to the surgical procedure and the tool identified by the machine learning system, and provide an indication when the determining indicates that the tool should be changed.

In various embodiments of the surgical guiding system, the information relating to the surgical procedure indicates tools which have been used for other surgical procedures of a same type as the surgical procedure, and in determining whether the tool should be changed, the instructions, when executed, cause the surgical guiding system to determine whether the tool is among the tools which have been used for the other surgical procedures.

In various embodiments of the surgical guiding system, in determining whether the tool should be changed, the instructions, when executed, cause the surgical guiding system to determine that the tool should be changed when the tool is not among the tools which have been used for the other surgical procedures.

In various embodiments of the surgical guiding system, the endoscope is a stereo-endoscope, the at least one image includes at least one stereoscopic image, and the at least one stereoscopic image includes depth information relating to the tool and to tissue of the surgical site.

In various embodiments of the surgical guiding system, the instructions, when executed, further cause the surgical guiding system to determine orientation information for the tool by the machine learning system based on the at least one image.

In various embodiments of the surgical guiding system, the machine learning system was trained using tool orientation information for other surgical procedures of a same type as the surgical procedure.

In various embodiments of the surgical guiding system, the orientation information of the tool determined by the machine learning system indicates whether the tool should be re-oriented.

In various embodiments of the surgical guiding system, the instructions, when executed, further cause the surgical guiding system to determine position information for the tool by the machine learning system based on the at least one image.

In various embodiments of the surgical guiding system, the machine learning system was trained using tool position information for other surgical procedures of a same type as the surgical procedure.

In various embodiments of the surgical guiding system, the position information for the tool determined by the machine learning system indicates whether the tool should be re-positioned.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Laparoscopic surgeries use various sizes, types, shapes, and kinds of surgical tools during the surgical procedure. If an improper tool is used during the laparoscopic surgery, the results of the procedure may be incomplete or unsatisfactory. Further, if a tool is positioned too close to or too far from the target tissue, or oriented incorrectly, similar unsatisfactory results may occur. The present disclosure provides guidance to a clinician regarding a tool used in a surgical procedure and can provide guidance relating to whether a tool should be changed, whether a tool should be re-positioned, and/or whether a tool should be re-oriented. As described in more detail below, aspects of the present disclosure relate to a machine learning system which has been trained using data from other surgical procedures similar to the surgical procedure that is being performed. Such a machine learning system can supplement a clinician's experience and judgment based on data from other, similar surgical procedures.

Figure 1A:
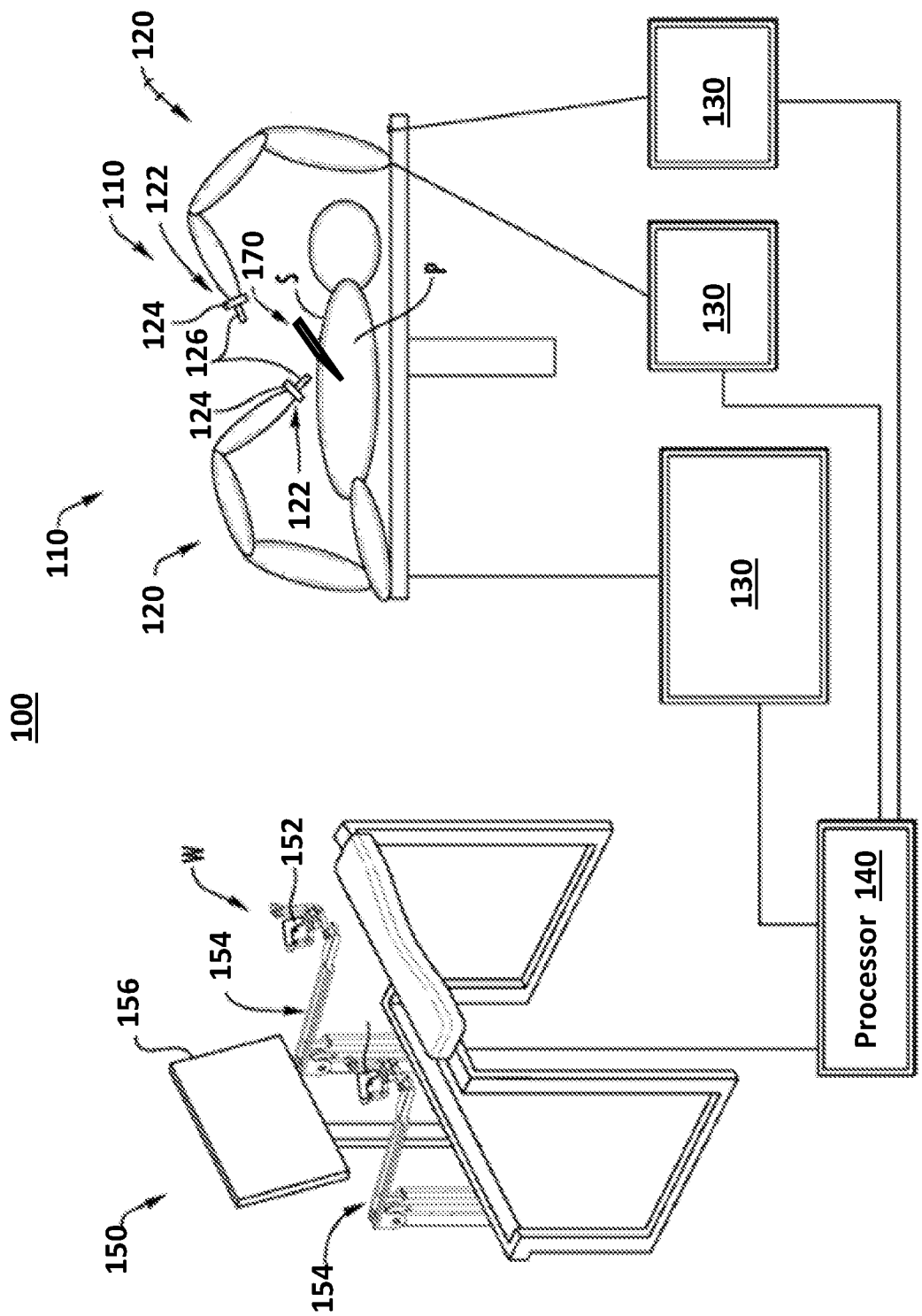
FIG. 1A is a perspective view of a surgical system in accordance with embodiments of the disclosure.
Figure 1B:
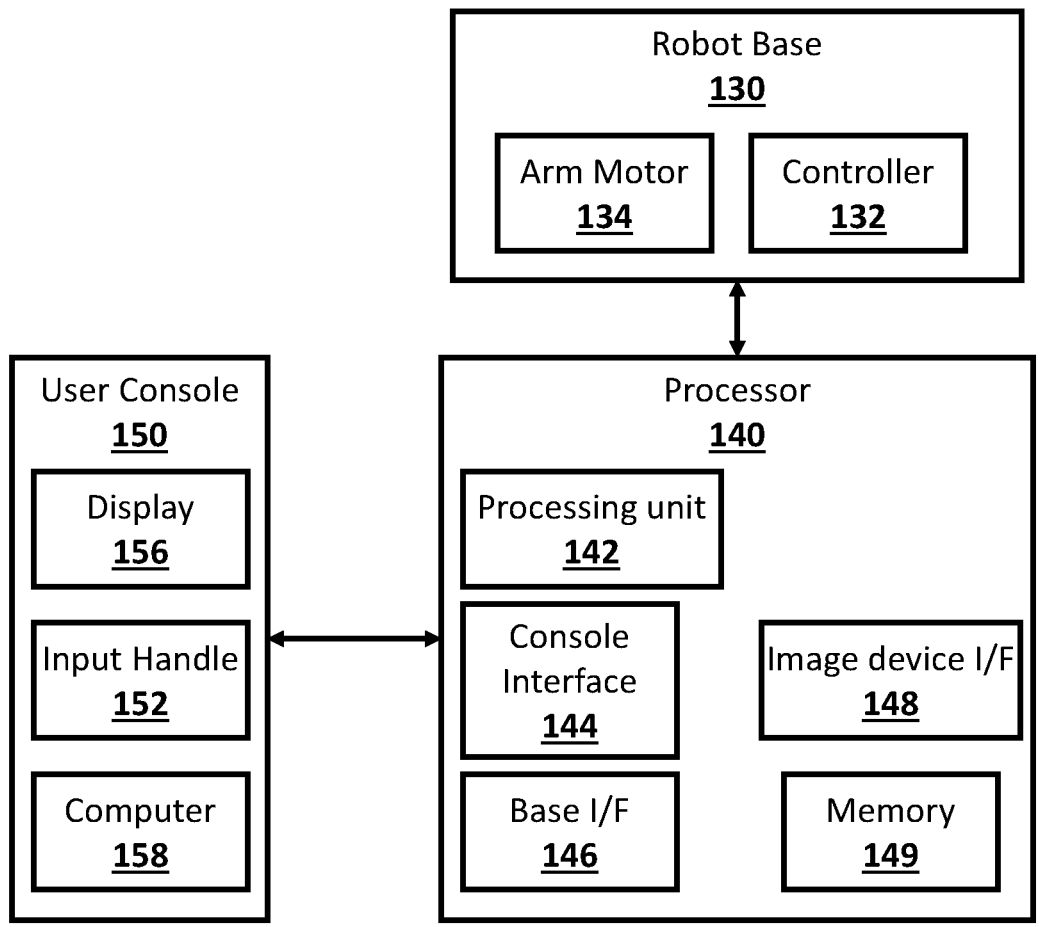
FIG. 1B is a functional block diagram of the surgical system of FIG. 1A in accordance with embodiments of the disclosure.

Referring to FIGS. 1A and 1B, a surgical system or robotic surgical system 100, in accordance with aspects of the disclosure, is shown and includes a surgical robot 110, a processor 140, and a user console 150. The surgical system 100 may not be able to completely conduct a surgery by itself and may be supplemented by a non-robotic tool 170. The surgical robot 110 includes one or more robotic linkages or arms 120 and robot bases 130 which support the corresponding robotic linkages 120. Each robotic linkage 120 moveably supports an end effector or tool 126, which is configured to act on a target of interest. Each robotic linkage 120 has an end 122 that supports the end effector or tool 126. In addition, the ends 122 of the robotic linkages 120 may include an imaging device 124 for imaging a surgical site "S".

The user console 150 is in communication with the robot bases 130 through the processor 140. In addition, each robot base 130 may include a controller 132, which is in communication with the processor 140, and an arm or robot arm motor 134, as shown in FIG. 1B. The robotic linkage 120 may include one or more arms, and joints between two adjoining arms. The arm motor 134 may be configured to actuate each joint of the robotic linkage 120 to move the end effector 126 to a proper position.

The non-robotic tool 170 or an end effector 126 may be inserted to the surgical site "S" to assist or perform the surgery during the surgical operation. In accordance with aspects of the present disclosure, in order to reduce occurrences of inappropriate tools being used during the surgery, the processor 140 may determine whether the inserted non-robotic tool 170 or the end effector 126 is appropriate. When it is determined that the tool is inappropriate, the processor 140 may display a popup window on a display device 156 of the user console 150 to provide an indication that the tool may be inappropriate. The indication is presented in a manner that does not interfere with the surgery.

In accordance with aspects of the present disclosure, and as described in more detail below, the processor 140 can determine when the tool is not properly positioned, such as being too far from or too close to a target organ for the surgery, when the tool is not properly oriented, such as being oriented with respect to the target at an inappropriate angle, or when the velocity of the tool is too fast to the target. An indication may be presented to bring these determinations to the clinician's attention. In various embodiments, the indication may include, but is not limited to, an audible sound, a popup window on the screen of the display 156, and/or vibrations to the input handles 152 of the user console 150.

Now referring to FIG. 1B, the processor 140 may be a stand-alone computing device similar to the computing device 200 of FIG. 2, or integrated into one or more components of the surgical system 100 (e.g., in the robot bases 130 or the user console 150). The processor 140 may also be distributed across multiple components of the surgical system 100 (e.g., in multiple robot bases 130.) The processor 140 of the surgical system 100 generally includes a processing unit 142, a memory 149, the robot base interface 146, a console interface 144, and an image device interface 148. The robot base interface 146, the console interface 144, and the image device interface 148 communicate with the robot bases 130, the user console 150, the imaging devices 162 via wireless configurations, e.g., Wi-Fi, Bluetooth, LTE, and/or wired configurations. Although depicted as a separate module, the console interface 144, the robot base interface 146, and the image device interface 148 may be a single component in various embodiments.

The user console 150 also includes input handles 152 which are supported on control arms 154 and which allow a clinician to manipulate the surgical robot 110 (e.g., move the robotic linkages 120, the ends 122 of the robotic linkages 120, and/or the tools 126). Each of the input handles 152 is in communication with the processor 140 to transmit control signals thereto and to receive feedback signals therefrom. Additionally or alternatively, each of the input handles 152 may include input devices (not explicitly shown) which allow the surgeon to manipulate (e.g., clamp, grasp, fire, open, close, rotate, thrust, slice, etc.) the tools 126 supported at the ends 122 of the robotic linkages 120.

Each of the input handles 152 is moveable through a predefined workspace to move the ends 122 of the robotic linkages 120, e.g., tools 126, within the surgical site "S". As the input handles 152 are moved, the tools 126 are moved within the surgical site "S" as detailed below. Movement of the tools 126 may also include movement of the ends 122 of the robotic linkages 120 which support the tools 126.

Figure 2A:
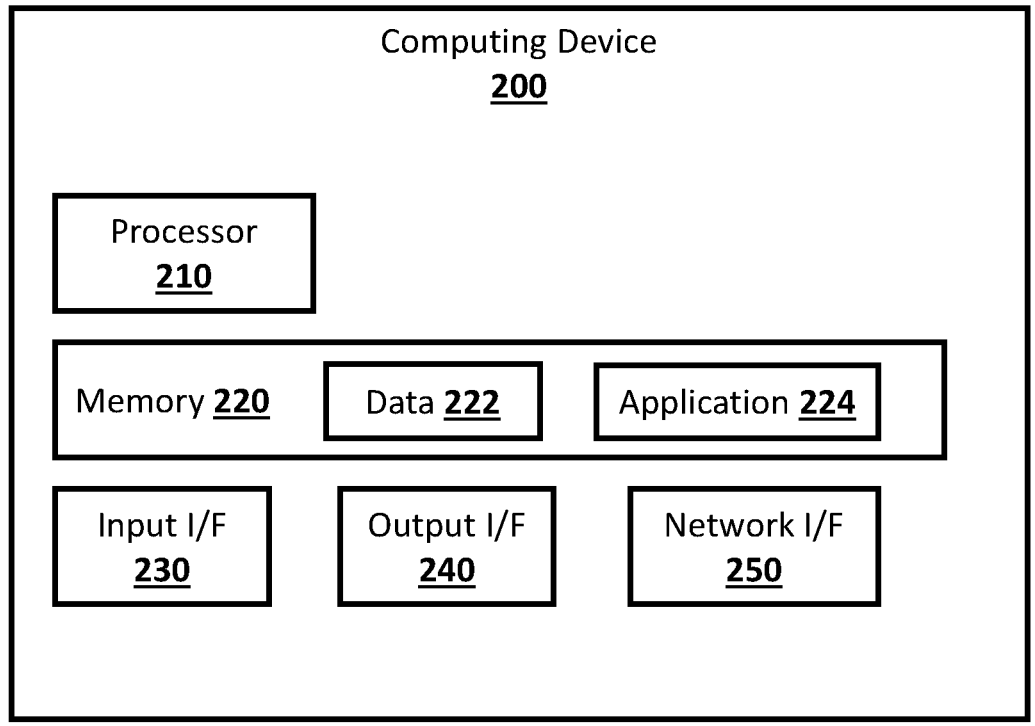
FIG. 2A is a functional block diagram of a computing device in accordance with embodiments of the disclosure.

The user console 150 further includes a computer 158, which includes a processing unit or processor and memory, which includes data, instructions and/or information related to the various components, algorithms, and/or operations of the robot bases 130, similar in many respects to the computing device 200 of FIG. 2A. The user console 150 may operate using any suitable electronic service, database, platform, cloud, or the like. The user console 150 is in communication with the input handles 152 and a display 156. Each input handle 152 may, upon engagement by the clinician, provide input signals to the computer 158 corresponding to the movement of the input handles 152. Based on the received input signals, the computer 158 may process and transmit the signals to the processor 140, which in turn transmits control signals to the robot bases 118 and the devices of the robot bases 118, to effect motion based at least in part on the signals transmitted from the computer 158. In various embodiments, the input handles 152 may be implemented by another mechanism such as handles, pedals, or computer accessories (e.g., a keyboard, joystick, mouse, button, touch screen, switch, trackball, and the like).

The user console 150 includes the display device 156 configured to display two-dimensional and/or three-dimensional images of the surgical site "S," which may include data captured by the imaging devices 124 positioned on the ends 122 of the robotic linkages 120. In various embodiments, the imaging devices 124 may capture stereoscopic images, visual images, infrared images, ultrasound images, X-ray images, thermal images, and/or other images of the surgical site "S". The imaging devices 124 transmit captured imaging data to the processor 140 which creates display screens of the surgical site "S" from the imaging data and transmits the display screens to the display device 156 for displaying such.

The display device 156 may be connected to an endoscope installed on the end 122 of the robotic arms 120 so that live view images from the endoscope may be displayed on the display device 156. Further, as described above, a potential notification may be displayed in an overlaying or overlapping manner over the live view images. The endoscope may capture images of the non-robotic tool 170 or the end effector 126. Such captured images of the tools 170 or 126 may be transmitted to and processed by the processor 140, which serves as or coordinates with a machine learning system to identify the tool 170 or 126. In accordance with aspects of the present disclosure, such information may be used to determine whether or not the surgery is appropriately performed.

The identification of the tool may be performed by a machine learning system based on one or more images. The identified tool can be compared with information relating to the surgical procedure to determine whether or not the tool is appropriate for the surgery. In other words, it is determined whether or not the identified tool should be moved or changed. For example, the machine learning system can identify the tool and various aspects of the tool such as size and shape. In case the tool is determined to be inappropriate in size, shape, and/or type for the surgery, an indicator can indicate that the tool should be changed. Further, in aspects of the present disclosure, the machine learning system can predict whether the tool is properly positioned or oriented. In these cases, an indicator can indicate whether the tool should be moved to a different position or orientation. The machine learning system may be trained based on training data derived from previously performed surgeries. The previously performed surgeries may be related to the current surgery being performed. For example, the training data can include frame images and tagged information, which are used to train the machine learning system to identify a tool, determine whether an orientation of a tool is appropriate, and/or whether a positioning of a tool is appropriate. In an aspect, the tagging of the training may be manually entered by doctors, experts, or medical professionals of the previous surgeries.

The tagged information may identify the tool captured in the frame images and/or may indicate whether a tool captured in frame images of the previous surgeries is appropriately positioned or oriented, such as whether the tool is too far or too close from target tissue, and/or oriented at an appropriate or an incorrect angle with respect to target tissue, among other things. The machine learning system may process the frame images with the tagged information to train the machine learning system to make determinations based on the images which will match the tagged information. Further, the machine learning system may be trained to identify a progression stage during the current surgery based on the frame images and/or tagged information of the previous surgeries, which are related to the current surgery.

Regarding the machine learning system, previous surgery videos or frame images may be used to train the machine learning system. For example, doctors or medical professionals may tag tools, organs, and progression information of the surgery in each video or in frame images. Specifically, medical professionals may tag a tool and a target organ in each frame image or video. In addition, they may also tag a frame image with a label of "too close" meaning that the tool is too close to the target organ in the image, or "too far" meaning that the tool is too far from the target organ in the image. This tagged information may be used to train the machine learning system to determine whether the tool captured in the frame images should be moved to a different location or orientation.

Further, medical professionals may also tag the tool on the image frames as being "inappropriate," meaning that the type, size, or shape of the tool is not appropriate for the respective surgical stage or progression. This tagged information may be used to train the machine learning system to predict whether a tool captured in the frame images should be changed.

Furthermore, medical professionals may also tag non-target but critical organs in the image frames so as to determine whether or not the non-target but critical organs are too close to the tool. As such, unintended contact with critical non-target organs may be reduced.

In an aspect, the machine learning system may process images or videos of previously performed surgeries and add tagged information of tools and progression stages. Such tagged information may be reviewed by experts, doctors, or medical professionals so that they confirm or revise the tagged information.

Referring now to FIG. 2A, a functional block diagram of a computing device is shown and designated generally as a computing device 200. Though not explicitly shown in the corresponding figures of the present application, the computing device 200, or one or more components thereof, may represent one or more components (e.g., the processor 140 or the computer 158) of the surgical system 100. The computing device 200 may include one or more processors 210, memories 220, input interfaces 230, output interfaces 240, network interfaces 250, or any desired subset of components thereof.

The memory 220 includes non-transitory computer-readable storage media for storing data and/or software which include instructions that may be executed by the one or more processors 210. When executed, the instructions may cause the processor 210 to control operation of the computing device 200 such as, without limitation, reception, analysis, and transmission of sensor signals received in response to movement and/or actuation of the one or more input handles 152. The memory 220 may include one or more solid-state storage devices such as flash memory chips. Additionally, or alternatively, the memory 220 may include one or more mass storage devices in communication with the processor 210 through a mass storage controller and a communications bus (not shown). Although the description of computer readable media described in this disclosure refers to a solid-state storage device, it will be appreciated by one of ordinary skill that computer-readable media may include any available media that can be accessed by the processor 210. More particularly, the computer readable storage media may include, without limitation, non-transitory, volatile, non-volatile, removable, non-removable media, and the like, implemented in any method of technology for storage of information such as computer readable instructions, data structures, program modules, or other suitable data access and management systems. Examples of computer-readable storage media may include RAM, ROM, EPROM, EEPROM, flash memory, or other known solid state memory technology, CD-ROM, DVD, Blu-Ray, or other such optical storage, magnetic cassettes, magnetic tape, magnetic disk storage or other magnetic storage devices, or any other medium which may be used to store information and which can be accessed by the computing device 200.

In embodiments, the memory 220 stores data 222 and/or one or more applications 224. Such applications 224 may include instructions which are executed on the one or more processors 210 of the computing device 200. The data 222 may include standard of care for surgeries, where the standard of care may include progression stages of each surgery and appropriate tools at each progression stage. Further, the standard of care saved in the data 222 may be updated or refined by surgeries performed in the future. Furthermore, the standard of care may be updated by a group of expert clinicians for each surgery.

The applications 224 may include instructions which cause an input interface 230 and/or an output interface 240 to receive and transmit sensor signals, respectively, to and from the various components of the surgical system 100. Additionally or alternatively, the computing device 200 may transmit the signals for analysis and/or display via the output interface 240. For example, the memory 220 may include instructions which, when executed, generate a depth map or point cloud of the objects within the surgical environment based on the real-time image data received from the image devices of the surgical system 100. The depth map or point cloud may be stored in the memory 220 across multiple iterations for a later cumulative analysis of the depth maps or point clouds.

Further, the applications 224 may include a machine learning algorithm and the computing device 200 may function as a machine learning system, which is trained with previous surgical videos/frame images with associated tagged information.

Figure 2B:
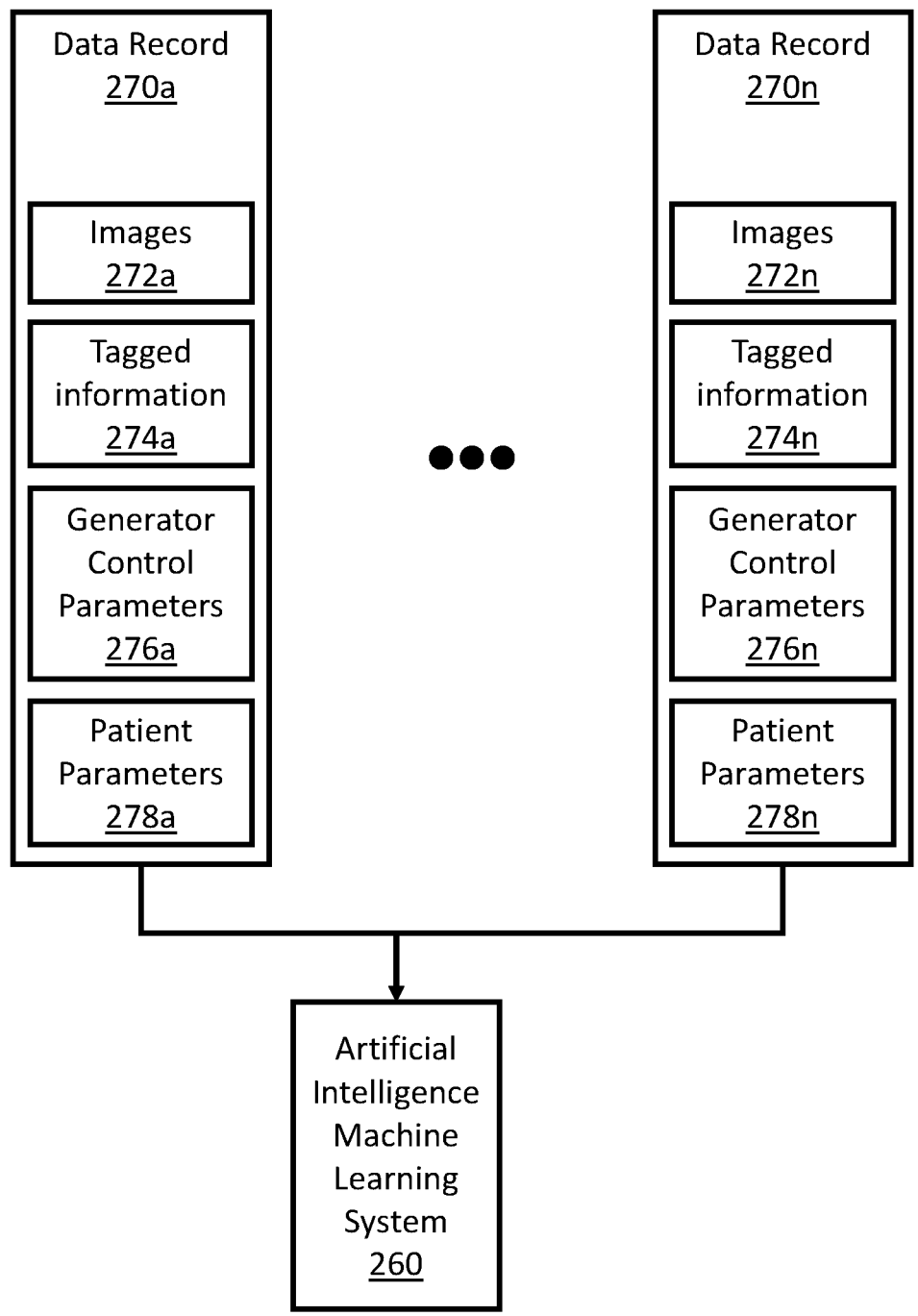
FIG. 2B is a block diagram of a machine learning system in accordance with embodiments of the disclosure.

Now referring to FIG. 2B, provided is a block diagram of a machine learning system 260, which may be implemented by the computing device 200 of FIG. 2A. The machine learning system 260 may be trained by a plurality of data records 270a-270n. Videos and frame images of previous surgeries may form one set of the data records. For example, the data record 270a may include frame images/videos 272a, tagged information 274a associated with the frame images 272a, and, if relevant, control parameters 276a for a generator which provided surgical energy for a surgery. In an aspect, one surgery may be divided into several stages. In this case, the data record 270a may include a plurality of sets of the data record 270a, and each set may include frame images, tagged information, and control parameters for the corresponding generator, for one stage. In another aspect, each stage may be considered to be separate from the other stages. As such, one surgery may result in two or more sets of the data records.

For simplicity, one letter (e.g., a-n) affixed to the end of a numeral may be omitted hereafter unless such is necessary. For example, the tagged information 274 may represent one or more of the tagged information 274a-274n. The tagged information 274 may be manually or automatically added to or embedded in the frame images 272. For example, medical professionals may manually tag information in the frame images 272 or a tagging algorithm may process the frame images 272 and automatically tag information in the frame images 272.

In another aspect, the frame images 272, the tagged information 274, the control parameters 276 for the generator, and patient parameters 278 of a previously performed surgery generates one data record 270. One data record 270 may be separate, independent from another of the plurality of data records 270a-270n generated from other surgeries.

The machine learning system 260 may be trained by the plurality of the data records 270a-270n. In an aspect, the machine learning system 260 may be trained with data records, which have been generated from surgeries similar to the current surgery. In this case, the machine learning system 260 may be trained by a supervised or reinforcement learning method. In case when the plurality of data records 270a-270n are generated from various surgeries, the machine learning system 260 may be trained by unsupervised learning. In another aspect, the machine learning system 260 may include, but not limited to, convolutional neural networks, recurrent neural networks (RNN), Bayesian Regression, Naive Bayes, nearest neighbors, least squares, means, and support vector regression, among other data science and artificial science techniques.

The tagged information 274 may have one or more levels. The first level is global, meaning that the tagged information in the first level is effective throughout the entire video or image frames, and the second level is local, meaning that the tagged information in the second level is effective for a portion of the video or the frame images. The first level information may include a type of surgery, a target organ, a position of the target organ, and a surgery plan including a range of appropriate surgery angles. The second level information may include tool information and progression information. The progression information may indicate what stage of the surgery is in corresponding frame images. The tool information may provide whether or not a tool is appropriate in size, shape, and type during the surgery, whether or not the tool is too close to or too far from the target organ for the surgery, whether or not the tool is approaching the target organ in an appropriate angle, and whether or not the tool is approaching toward the target organ too fast. In an aspect, the tool information may provide whether or not the tool is too close to a critical non-target organ during the surgery.

Doctors, experts, or medical professionals may add the tagged information 274 to the frame images 272. For example, a tool may be tagged with the boundaries of the tool in the frame images 272. The target organ and a non-target critical organ may be tagged in the same way as the tool. Positional information and/or orientation information about the tool, such as "too far," "too close," "wrong angle," "too fast," etc., may be added to the frame images 272. The machine learning system 260 may process the images 272 with the associated or corresponding tagged information 274, adjust, update, and revise internal control parameters of the machine learning system 260, and store the internal control parameters in a configuration file.

In embodiments, the tagged information 274 may further include surgical procedural information related to the surgical operation. The surgical procedural information may indicate relationship between the tool and the tissue. For example, the tool may include two jaw members and the surgical procedural information may indicate how much tissue is grasped between the two jaw members. Further, the surgical procedural information may include how hard the two jaw members press the tissue.

In a case when the tool is a cutter, the surgical procedural information may indicate how deep the cut was made by the cutter.

The surgical procedural information may further include hemodynamics during the surgery. During tissue dissection or tissue approximation, bleeding might occur. The surgical procedural information may indicate whether or not bleeding occurred or how much bleeding has occurred.

Furthermore, other information related to the surgical operation may be tagged so that the machine learning system 260 may be trained with these pieces of tagged information.

The generator control parameters 276 may be parameters for a generator which is to supply surgical energy for the surgery, and include, but not limited to, for example, duration, power, ramp rate, frequency, or other generator parameters for the surgery. The generator control parameters 276 may be saved in a database or memory because it is not likely the generator control parameters 276 can be acquired or obtained from processing the frame images 272.

The data records 270 may further include patient parameters 278. The patient parameters 276 may include a patient's age, tissue moisture, hydration, and/or tissue location within the patient's body, among other patient characteristics. In various embodiments, the data relating to the patient parameters 278 may be entered into the data records 270 manually or automatically from the patient's medical records. Since the patient parameters 278 may not be acquired from image processing of the images 272, the patient parameters 278 may be saved in a database or memory as the generator control parameters 276.

After processing and learning from the data records 270 generated from the previous surgeries, the machine learning system 260 is then able to process real-time frame images/videos of a current surgery and provide notifications based on the results. For example, when one or more real-time frame images show that a tool is too close to the target organ, the machine learning system 260 may present an indication that a tool is too close to the target organ for the surgery. Or when one or more real-time frame images show that the tool is approaching to the target organ in a wrong angle, the machine learning system 260 may present an indication that the tool is approaching to the target from a wrong angle. In a similar way, when one or more frame images show that the tool is approaching too fast to the target organ, the machine learning system 260 may present such an indication.

Now referring back to FIG. 2A, the output interface 240 may further transmit and/or receive data via a network interface 250 via one or more wireless configurations, e.g., radio frequency, optical, Wi-Fi®, Bluetooth® (an open wireless protocol for exchanging data over short distances, using short length radio waves, from fixed and mobile devices, creating personal area networks (PANs), ZigBee® (a specification for a suite of high level communication protocols using small, low-power digital radios based on the IEEE® 802.15.4-2003 standard for wireless personal area networks (WPANs)). Although depicted as a separate component, the network interface 250 may be integrated into the input interface 230 and/or the output interface 240.

Figure 3:
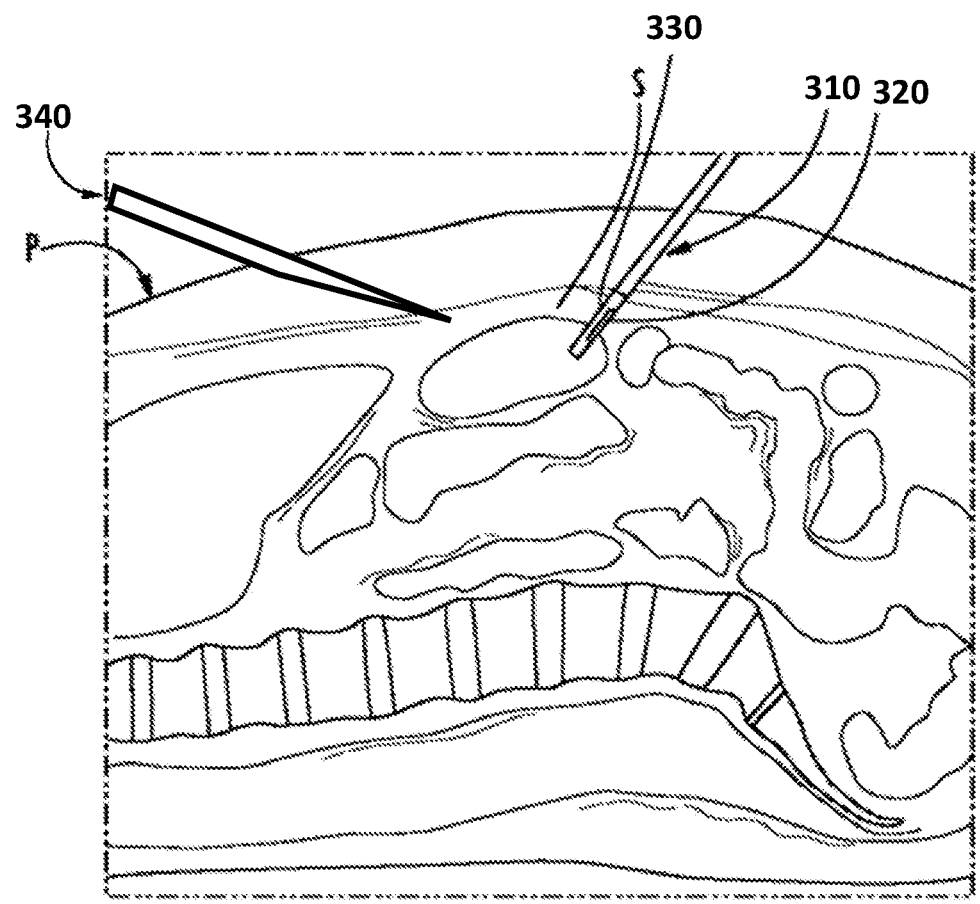
FIG. 3 is a graphical illustration of a surgical image to be processed by a machine learning system in accordance with embodiments of the disclosure.

With additional reference to FIG. 3, the surgery system 100 of FIG. 1A may include an endoscope 310, which is inserted through a body cavity of the patient "P" and is configured to provide optical views or frame images of the surgical site "S" and to transmit the frame images to the display device 156. The endoscope 310 includes a camera 320 to capture images of the surgical site "S" and a tool 340 during a surgery as detailed below. The camera 320 may be an ultrasonic imaging device, a laser imaging device, a fluorescent imaging device, or any other imaging device, which is capable of producing real-time frame images. In various embodiments, the endoscope 310 may be a stereo-endoscope which captures stereo-images having depth information.

The endoscope 310 is inserted through an opening, either a natural opening or an incision, to position the camera 320 within the body cavity adjacent the surgical site "S" to allow the camera 320 to capture images of the surgical site "S" and the tool 340. The camera 320 transmits the captured images to the machine learning system 260 of FIG. 2B. The machine learning system 260 receives the captured images of the surgical site "S" from the camera 320 and displays the received images on a display device such that the clinician can visually see the surgical site "S" and the tool 340. The endoscope 310 may include a sensor 330 that captures the pose of the camera 320 when the images of the surgical site "S" are captured. The sensor 330 is in communication with the machine learning system 260 such that the machine learning system 260 receives the pose of the camera 320 from the sensor 330 and associates the pose of the camera 320 with the images captured by the camera 320.

In an aspect, the machine learning system 260 may process the images and may identify a type, shape, and size of the tool 340 in consideration of the pose of the camera.

The machine learning system 260 may also be trained to identify progression stages of the surgery from the real-time frame images, which may have been refined by a plurality of images of the previous surgeries, which are related to the current surgery.

The identified progression stages may include navigation to the target organ, identification of the target region, entry of preparatory tools for the surgery to the target organ, performance of the surgery, confirmation of completeness of the surgery, and retreat of all tools from the target organ. The list of progression stages is provided as an example but not limited thereto.

Based on the identified progression stage, the machine learning system 260 may identify whether or not the tool 340 is appropriate in type, shape, and size according to the identified progression stage. In case the tool 340 does not have a proper type, shape, or size, the machine learning system 260 may provide an indication that the tool 340 is not appropriate in type, shape, or size based on the identified progression stage. In various embodiments, a tool identified by the machine learning system 260 may be compared to a database of tools used in other similar surgeries. If the tool identified by the machine learning system 260 is not among the tools used in other similar surgeries, a notification can be provided to indicate that the tool should be changed.

In an aspect, the notification may indicate that the type of the tool is appropriate for the surgery but the size thereof is too large or too small for proper operations in the identified progression stage, or that the tool is inappropriate for the identified progression stage. The notification may be generally made in a manner that does not interfere with the surgery. If the level of potential harm from using the tool 340 appears imminent or severe, the notification may be presented with heightened alerts, such as red flashes on the screen, haptic vibrations on the input handle 152 of FIG. 1, or audible alert sounds.

Further, based on the frame images, the machine learning system 260 may identify whether a pose or orientation of the tool 340 is appropriate or incorrect. In case the orientation of the tool 340 is determined to be incorrect or inappropriate by the machine learning system 260, the notification can indicate the tool should be re-oriented or re-positioned.

The machine learning system 260 may record the determinations and notifications during the surgery for further refinement of the internal control parameters of the machine learning system 260 in the future. For example, the surgeon who has performed the surgery or a group of experts may tag information over the frame images in consideration of the notifications. They may discuss the efficacy of the tool used in the surgery, and refine or update the tagged information of the tool from "inappropriate" to "appropriate" based on the positive efficacy in the surgery or vice versa. The machine learning system 260 may be trained with these updates and further refine internal control parameters saved in a configuration file.

Figure 4:
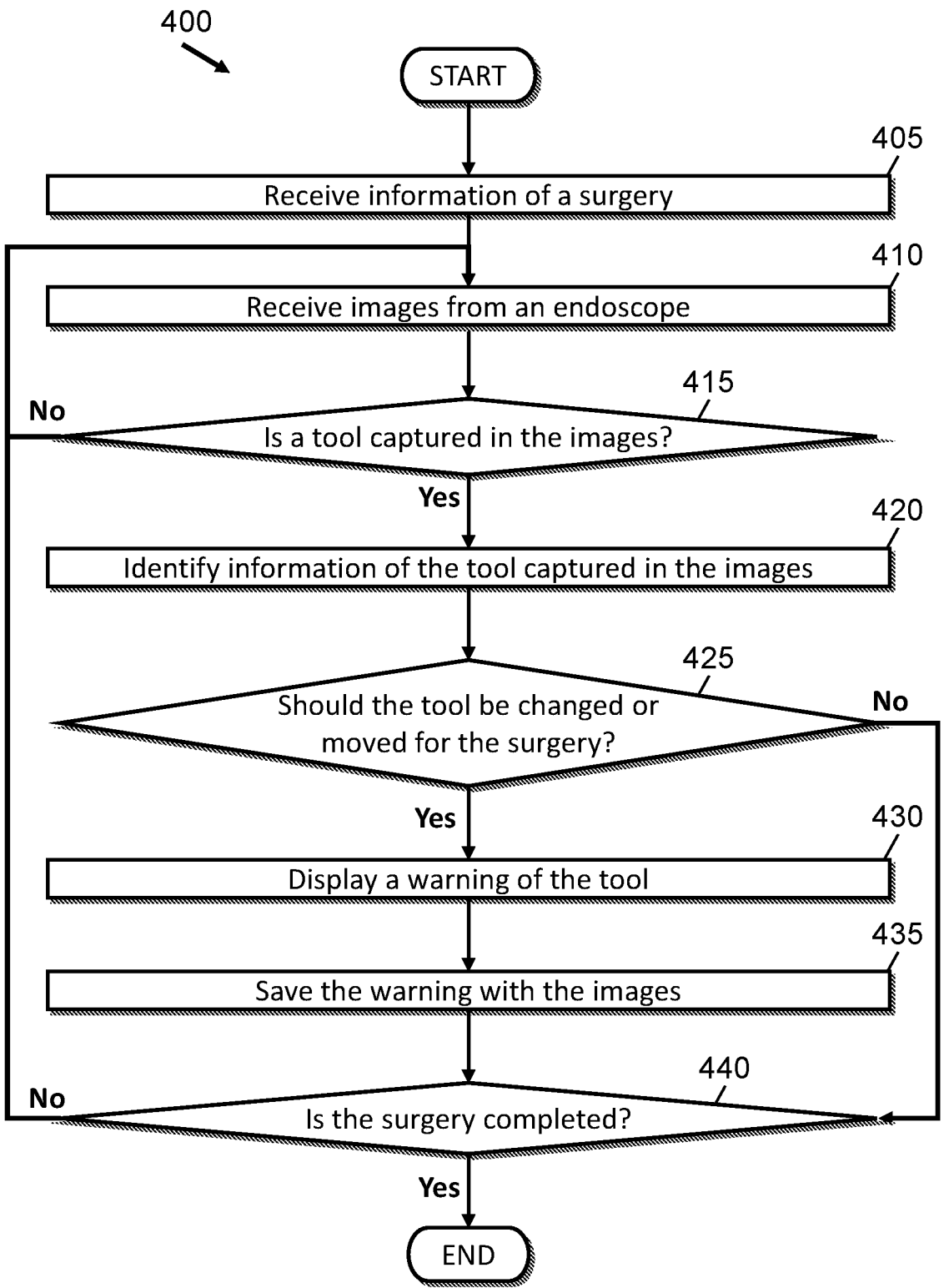
FIG. 4 is a flowchart illustrating a method for checking whether a tool should be moved or changed during a surgery in accordance with the disclosure.

FIG. 4 is a flowchart illustrating a method 400 for checking whether or not a tool captured in images is appropriate during a surgery in accordance with embodiments of the disclosure. When a surgical tool or instrument is inserted into an orifice of a patient, one or more cameras (e.g., a stereoscopic endoscope) may capture images of the tool or instrument and a surgical site. The method 400 starts by receiving information of the surgery in step 405. The information of the surgery includes a type of surgery, a target organ, and a position of the target organ. The information of the surgery may be manually or automatically retrieved from a database stored in a memory, which is entered by a doctor or medical professional.

A machine learning system may be configured for the current surgery based on the information of the current surgery. The machine learning system may save a separate configuration file for different types of surgical procedures. In an aspect, the machine learning system may retrieve a configuration file, which is used to process images of the current surgery.

In step 410, images of the surgical site are received from the endoscope by the machine learning system. The images are processed to determine whether the tool is captured in the images in step 415. This determination may be performed by an image processing algorithm or by the machine learning system.

In a case when it is determined that the tool is not captured in the images in step 410, the method 400 returns to step 410 until the tool is captured in the images.

When the tool is determined to be captured in the images, the information of the tool is identified by the machine learning system from the images in step 420. The information of the tool may include a size, shape, position information, and orientation information of the tool. In an aspect, the pose of an endoscope or a camera, which has captured the images, may be also considered to adjust the images so that the machine learning system can identify the tool with accuracy. In step 420, the machine learning system may also identify a target organ.

In embodiment, hemodynamics may be also determined in step 420. For example, it is determined whether or not bleeding occurred and, if so, how much bleeding has occurred. Further, relationship between the tool and the tissue may also be determined in step 420. The amount of tissue grasped by two jaw members of the tool may be determined. Also, the amount of pressure applied by the two jaw members may be determined. When such determination is determined in step 425 to be out of a range suitable for the surgical operation, a warning about the surgical operation may be displayed in step 430.

In step 425, the machine learning system determines whether or not the tool should be changed or re-positioned or re-oriented based on the configuration file, which has been generate, revised, and updated by images of previous surgeries by the machine learning system. If the machine learning system determines that the tool should be moved or changed, the method 400 proceeds to step 440.

When it is determined that the tool should be changed in step 425, meaning that the tool is inappropriate in shape or size or type for the surgery, the corresponding indication is displayed for the surgeon in step 430. In particular, the notification brings the surgeon's attention that the tool does not have a type, size, or shape suitable for the surgery and should be changed or replaced.

When it is determined that the tool should be re-oriented in step 425, meaning that the tool is positioned in a wrong orientation relative to the target organ for the surgery, an indication is display so that the tool is re-oriented.

Determination that the tool should be moved in step 425 may also mean the tool is not appropriately positioned relative to the target organ for performing the surgery. In this case, the indication is presented so that the surgeon re-positions the tool.

Further, determination that the tool should be moved in step 425 may also mean the tool is approaching the target organ too fast. In this case, the indication is presented so that the surgeon slows down the speed of the tool toward the target organ.

In an aspect, the warning may be relayed to the clinician via haptic vibrations or audible sound alerts. In a case when the level of inappropriateness is sufficiently high to outweigh against performing the surgery, the operation may be abruptly stopped to mitigate potential harms.

In step 435, the detected tool with the images may be recorded for future reference. For example, a board of experts may gather together to enter, refine, or update tagged information for this surgery based on the warning records, and the machine learning system can train itself with this new data. In this way, the machine learning system may update and refine the internal control parameters and save in the configuration file.

In step 440, it is determined whether or not the surgery is completed. When the surgery is not complete, the method 400 reiterates steps 410-440. Otherwise, the method 400 is ended after completion of the surgery.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A method for guiding a surgical procedure, the method comprising:
   accessing information relating to a surgical procedure;
   accessing at least one image of a surgical site captured by an endoscope during the surgical procedure;
   identifying a tool captured in the at least one image by a machine learning system;
   determining whether the tool should be moved based on comparing the information relating to the surgical procedure and the tool identified by the machine learning system; and
   providing an indication:
      when the determining indicates that the tool should be moved; and
      when the tool is moving toward a target organ tissue at a speed that is greater than a predetermined speed.

2. The method according to claim 1, wherein the information relating to the surgical procedure indicates tools which have been used for other surgical procedures of a same type as the surgical procedure, and wherein the method further comprises:
   determining whether the tool should be changed based on comparing the information relating to the surgical procedure and the tool identified by the machine learning system;
   wherein determining whether the tool should be changed includes determining whether the tool is among the tools which have been used for the other surgical procedures.

3. The method according to claim 2, wherein determining whether the tool should be changed includes determining that the tool should be changed when the tool is not among the tools which have been used for the other surgical procedures.

4. The method according to claim 1, wherein the endoscope is a stereo-endoscope, the at least one image includes at least one stereoscopic image, and the at least one stereoscopic image includes depth information relating to the tool and to tissue of the surgical site.

5. The method according to claim 4, further comprising determining position information for the tool by the machine learning system based on the at least one image.

6. The method according to claim 5, wherein the machine learning system was trained using tool position information for other surgical procedures of a same type as the surgical procedure.

7. The method according to claim 6, wherein the position information for the tool determined by the machine learning system indicates whether the tool should be re-positioned.

8. The method according to claim 4, further comprising determining orientation information for the tool by the machine learning system based on the at least one image.

9. The method according to claim 8, wherein the machine learning system was trained using tool orientation information for other surgical procedures of a same type as the surgical procedure.

10. The method according to claim 9, wherein the orientation information for the tool determined by the machine learning system indicates whether the tool should be re-oriented.

11. A surgical guiding system for guiding a surgical procedure, the system comprising:
   a memory configured to store instructions; and
   a processor coupled with the memory and configured to execute the instructions to cause the surgical guiding system to:
      access information relating to a surgical procedure;
      access at least one image of a surgical site captured by an endoscope during the surgical procedure;
      identify a tool captured in the at least one image by a machine learning system;
      determine whether the tool should be moved based on comparing the information relating to the surgical procedure and the tool identified by the machine learning system; and
      provide an indication;
         when the determining indicates that the tool should be moved; and
         when the tool is moving toward a target organ tissue at a speed that is greater than a predetermined speed.

12. The surgical guiding system according to claim 11, wherein the information relating to the surgical procedure indicates tools which have been used for other surgical procedures of a same type as the surgical procedure, and wherein the method comprises:
   determining whether the tool should be changed based on comparing the information relating to the surgical procedure and the tool identified by the machine learning system;
   wherein in determining whether the tool should be changed, the instructions, when executed, cause the surgical guiding system to determine whether the tool is among the tools which have been used for the other surgical procedures.

13. The surgical guiding system according to claim 12, wherein in determining whether the tool should be changed, the instructions, when executed, cause the surgical guiding system to determine that the tool should be changed when the tool is not among the tools which have been used for the other surgical procedures.

14. The surgical guiding system according to claim 11, wherein the endoscope is a stereo-endoscope, the at least one image includes at least one stereoscopic image, and the at least one stereoscopic image includes depth information relating to the tool and to tissue of the surgical site.

15. The surgical guiding system according to claim 14, wherein the instructions, when executed, further cause the surgical guiding system to determine position information for the tool by the machine learning system based on the at least one image.

16. The surgical guiding system according to claim 15, wherein the machine learning system was trained using tool position information for other surgical procedures of a same type as the surgical procedure.

17. The surgical guiding system according to claim 16, wherein the position information for the tool determined by the machine learning system indicates whether the tool should be re-positioned.

18. The surgical guiding system according to claim 14, wherein the instructions, when executed, further cause the surgical guiding system to determine orientation information for the tool by the machine learning system based on the at least one image.

19. The surgical guiding system according to claim 18, wherein the machine learning system was trained using tool orientation information for other surgical procedures of a same type as the surgical procedure.

20. The surgical guiding system according to claim 19, wherein the orientation information of the tool determined by the machine learning system indicates whether the tool should be re-oriented.

* * * * *